United States Patent
Hall et al.

[11] Patent Number: 6,148,655
[45] Date of Patent: Nov. 21, 2000

[54] METHOD FOR CALIBRATING ULTRASOUND DEVICES AND CONTRAST AGENTS AND SYSTEM THEREFOR

[75] Inventors: Christopher S. Hall, St. Louis; Michael S. Hughes, Glencoe, both of Mo.

[73] Assignee: Mallinckrodt Inc., St. Louis, Mo.

[21] Appl. No.: 09/180,484

[22] PCT Filed: May 30, 1997

[86] PCT No.: PCT/US97/08803

§ 371 Date: Nov. 12, 1998

§ 102(e) Date: Nov. 12, 1998

[87] PCT Pub. No.: WO97/46159

PCT Pub. Date: Dec. 11, 1997

Related U.S. Application Data

[60] Provisional application No. 60/019,099, Jun. 3, 1996.

[51] Int. Cl.[7] .............................. G01N 29/00; A61B 8/00; A61B 8/14
[52] U.S. Cl. ............................... 73/1.83; 73/1.86; 424/9.5
[58] Field of Search .................................... 73/1.83, 1.86, 73/1.82; 600/458; 424/9.5

[56] References Cited

U.S. PATENT DOCUMENTS

| | | |
|---|---|---|
| 4,277,367 | 7/1981 | Madsen et al. .......................... 252/408 |
| 4,843,866 | 7/1989 | Madsen et al. . |
| 5,230,343 | 7/1993 | Guberek et al. ......................... 436/564 |
| 5,342,283 | 8/1994 | Good ............................................. 600/8 |
| 5,433,207 | 7/1995 | Pretlow, III ......................... 128/662.02 |
| 5,542,935 | 8/1996 | Unger et al. ............................. 604/190 |
| 5,874,062 | 2/1999 | Unger ........................................ 424/9.4 |
| 5,877,146 | 3/1999 | McKenzie et al. .......................... 514/6 |
| 5,886,245 | 3/1999 | Flax ........................................... 73/1.86 |
| 5,902,748 | 5/1999 | Madsen et al. .............................. 436/8 |
| 5,922,304 | 7/1999 | Unger ........................................ 424/9.3 |

FOREIGN PATENT DOCUMENTS

2571980 A1   4/1986   France .

*Primary Examiner*—Thomas P. Noland
*Attorney, Agent, or Firm*—Rothwell, Figg, Ernst & Manbeck, p.c.

[57] ABSTRACT

A method for calibrating ultrasound equipment and ultrasound contrast agents are provided that utilize polystyrene microspheres as a broad-band in vitro calibration tool. In accordance with the method a suspension of polystyrene microspheres is provided in a liquid environment in a container having an acoustic aperture. The suspension of microspheres is continuously agitated during measurement of the backscatter from the suspension of microspheres and the ultrasound equipment or contrast agent is then calibrated or adjusted to a selected backscatter setting.

8 Claims, 7 Drawing Sheets

METHOD FOR CALIBRATING ULTRASOUND DEVICES AND CONTRAST AGENTS AND SYSTEM THEREFOR

CROSS-REFERENCE TO RELATED APPLICATION

This application is the U.S. national stage application filed under 35 U.S.C. 371 of PCT/US97/08803, filed May 30, 1997 and published as WO97/46159 on Dec. 11, 1997 which claimed priority of U.S. provisional application no. 60/019,099 filed Jun. 3, 1996, the benefit of which is hereby claimed.

FIELD OF THE INVENTION

This invention relates in general to a method for calibrating diagnostic ultrasound equipment and ultrasound contrast agents and, more particularly, to a method of calibration with which to make absolute measurements of the backscatter and attenuation of tissue or contrast agents.

BACKGROUND OF THE INVENTION

The use of high frequency ultrasound for medical applications has been increasing in recent years with the advent of intravascular ultrasound, acoustic microscopy and second harmonic imaging with ultrasonic contrast agents. Higher frequencies allow new morphologic structures to be examined as well as opening a new area of ultrasonic tissue characterization. In the past, tissue characterization has been hampered by the lack of a standard method of calibration with which to make absolute measurements of the backscatter and attenuation of different types of tissue or contrast agents.

The current standard for calibration of diagnostic ultrasound equipment utilizes the reflection from a polished stainless steel plate. This procedure is disadvantageous because of its sensitivity to alignment of the surface of the plate and the fact that the reflection is much greater than that returned by tissue. The ultrasonic scatter from tissue is often modeled as a collection of scatterers suspended in a water-like medium. The use of calibration standards or "phantoms" that mimic tissue has been of particular interest to the tissue characterization community. Typically these phantoms consist of a collection of scatterers held in an agarose or gelatin-like media such as described in U.S. Pat. Nos. 4,843,866 and 4,277,367, the entirety of each being hereby incorporated by reference. A substantial body of work exists that examines phantoms for ultrasound in the frequency range below 5 MHz. The geometrical shape and physical parameters of the scatterers within tissue can be further derived with the use of an appropriate data reduction method. The use of gelbased phantoms are disadvantageous, however, in that many spatial site averages must be obtained to yield a stable result and requires substantial expertise to construct and maintain.

In the higher frequency world of acoustic microscopy and intra-vascular imaging, however, it is not clear whether the existing phantoms will provide a useful and reproducible method for calibration. There is, therefore, a need in the art for a broadband, in vitro method for calibration of diagnostic ultrasound equipment and for ultrasound contrast agents used therewith that substantially mimics the reflection returned by tissue, is easy to construct and maintain and removes the problems associated with alignment of the calibrating tool.

SUMMARY OF THE INVENTION

The present invention is directed to a method for calibrating diagnostic ultrasound equipment and ultrasound contrast agents is provided that utilizes polystyrene microspheres as a broadband in vitro calibration tool. In accordance with the method, a suspension of polystyrene microspheres are provided in a liquid environment in a container having an acoustic aperture. The suspension of microspheres is continuously agitated during measurement of the backscatter from the suspension of microspheres and the ultrasound equipment or contrast agent is then calibrated or adjusted to a selected backscatter setting.

In one significant aspect of the invention, the method comprises the steps of providing a suspension of microspheres in a liquid environment in a container having an acoustic aperture in a constant temperature water bath, continuously agitating the suspension of microspheres during measurement of the backscatter from the suspension of microspheres, and adjusting the ultrasound system to a selected backscatter setting. Following measurement of the backscatter, various functions such as mean backscatter, backscatter coefficient, backscatter transfer function, or mean backscatter transfer function may be calculated prior to the adjusting step.

DETAILED DESCRIPTION OF THE INVENTION

Figure 1:
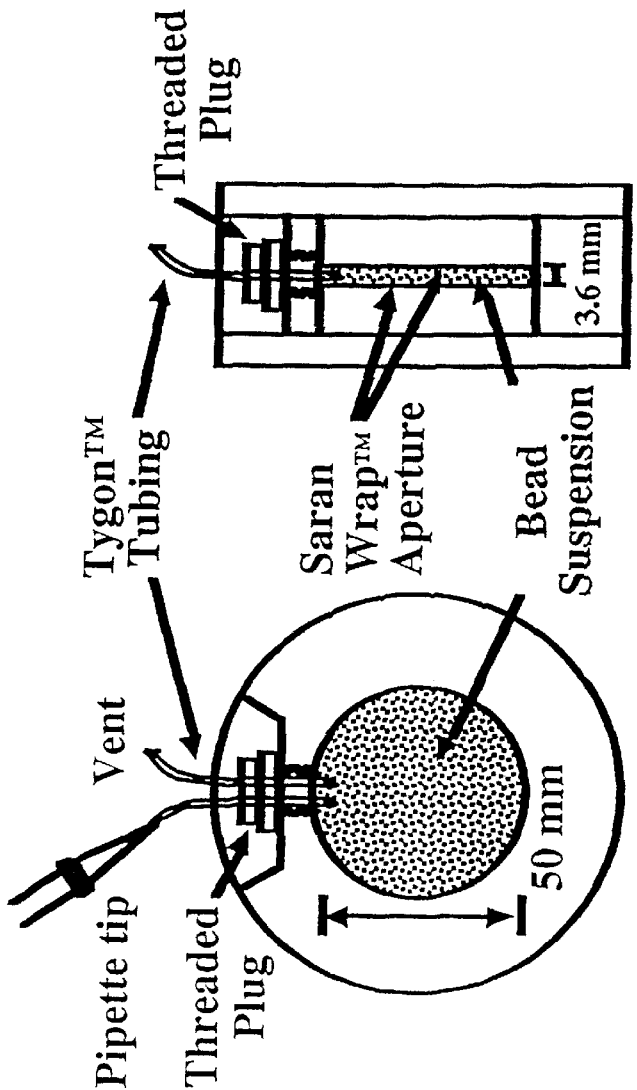
FIG. 1: A diagram of the specimen chamber used to hold and agitate the suspension of polystyrene microspheres.

In accordance with the present invention, it has been discovered that by utilizing a suspension of microspheres in a liquid environment and continuously agitating the suspension during measurement of the backscatter of the suspension, a useful method for calibrating diagnostic ultrasound equipment and ultrasound contrast agents is provided. The suspension may be continuously agitated by various means of agitation including manual and mechanical means, such as stirring, mixing, pumping, shaking and the like. Preferably, the suspension is continuously agitated by providing a means in communication with the container containing the suspension of microspheres in the liquid environment and providing a pumping means into the liquid that provides sufficient mixing and agitation of the microspheres to keep them in suspension at randomized locations during measurement of the backscatter of the suspension of microspheres. A suitable device for performing the calibration is shown in FIG. 1. In the specimen chamber shown in FIG. 1, a length of tubing is provided as a port into the container containing the suspension of microspheres and a pipette is attached thereto. The pipette is used to mix the suspension of microspheres by pumping the pipette vigorously during measurement of the backscatter. Other means for providing the mixing and agitation include the provision of a mechanical pump or stirring system in communication with the suspension of beads in the specimen chamber. The specimen chamber or container containing the suspension of beads has at least one acoustic aperture through which the backscatter measurement is taken. The acoustic aperture is a thin film that permits the transmission of ultrasonic energy with minimal distortion. It is used to contain the microsphere suspension during the calibration procedure. Suitable materials for forming the acoustic aperture include, polyethylene film (such as Saran Wrap) and mylar film, all less than 0.001 inch thick. The suspension of microspheres is provided in a liquid environment such as water, saline, alcohol, buffers, or other suitable liquids capable of providing a suspension of microspheres and being mixed. The liquid environment may optionally contain other components such as a surfactant. In one preferred embodiment, the liquid environment is comprised of a saline solution (Coulter™ Isoton II) and a surfactant. The calibration method of this invention is preferably performed in a constant temperature water bath to serve as the medium in which the ultrasound waves are propagated and to regulate the temperature of the microsphere suspension during the calibration procedure.

The microspheres useful in connection with the method of the present invention may be hollow or solid. Preferably, the microspheres are polystyrene microspheres obtained from Duke Scientific Corporation, CS03MC. The microspheres may be provided in a selected size distribution for the type of calibration is to be performed. This may be dependent upon the type of diagnostic ultrasound procedure is to be performed on an individual.

As the backscatter data from the suspension of microspheres is obtained in accordance with the method of the invention, the ultrasound device, system, apparatus, or equipment is calibrated by protocols known to those skilled in the art to a selected backscatter setting. Briefly, the method of the invention is performed and the appropriate settings on the ultrasound device being calibrated, such as the gain, swept gain, intensity, suppression level, frequency and the transducer, are fixed to a selected backscatter setting to provide optimal results for the diagnostic procedure being performed. As is understood by those skilled in the art, these settings are dependent upon the condition of the individual being tested, the tissue being tested, the use of a contrast agent, and the information desired to be obtained.

The scattering from solid spheres has been a topic of many avenues of research in acoustics. The first complete description of scattering from a solid sphere has been attributed to Faran. Solid plastic and metallic spheres in a fluid have provided a simple system with which to understand the physics of ultrasonic scattering in a wide variety of experiments. Early research was driven by interest in the effects of scatterers in sonar. An area of current interest is the use of the interaction between ultrasound and solid, elastic spheres to predict sedimentary transport processes in the marine environment. Previous measurements have yielded results for a wide range of ka where k is the wavenumber of insonifying ultrasound and a is the scatterer diameter. A major advantage to using agitated suspensions of elastic spheres is the inherent ensemble averaging due to the motion and distribution to scatterers within the suspension. Investigations of the attenuation of sound in suspensions and resonance scattering in suspensions have shown that increased backscatter cross-sections of up to five times the geometric cross-section can occur at frequencies corresponding to the rigid resonances and modal resonances of the spheres.

This study was designed to validate an experimental system used in the measurement of the physical properties of ultrasonic contrast agents. This system has been used previously to analyze the physical properties of Albunex® and other contrast agents. Plastic spheres were employed for several reasons: their shape is similar to most solid and gas bubble based contrast agents; the scatterers exhibit resonances, although for different physical reasons than do gaseous, microbubble, contrast agents; the plastic microspheres can be made in a similar size range to the agents; and it is possible to manufacture the suspension in a repeatable manner. All measurements were made with a single matched pair of transducers excited by a broadband pulse to obtain data from 5 to 35 MHz in a single measurement. To the knowledge of the authors, the use of a single transducer pair to obtain measurements over such a broad frequency bandwidth in a single pulse experiment is a novel approach. In previous measurements, researchers have used several sets of matched transducers in broadband pulse or swept frequency experiments.

The study was also designed to validate a simple, first-order, broadband reduction technique. This technique makes several simplifying approximations about the transducer's beam profile and the effects of time gating the signal. The well-controlled experimental system of a suspension of polystyrene spheres aided in testing the validity of these approximations. The data reduction technique is not computationally intensive and could be used in future in vivo tissue characterization applications.

Theory

The theoretical prediction of the scattering of sound from solid spheres is well known. The predictions of the scattering of sound from solid spheres can be obtained by solving the wave equation in three-dimensions and using the physical boundary conditions of the material of the solid sphere. The three relevant boundary conditions are i) the pressure in the fluid must be equal to the normal component of stress in the solid at the interface; ii) the normal (radial) component of the displacement of the fluid must be equal to the normal component of the displacement of the solid; iii) the tangential components of shearing stress must vanish at the surface of the solid.

Using these boundary conditions and the wave equation, it is possible to derive an exact expression for the scattering from a sphere due to an incident plane wave. The far-field expression for the pressure due to scattering from a sphere is $$P = \frac{P_0}{kr}\left|\sum_{n=0}^{\infty}(2n+1)\sin\delta_n \exp(i\delta_n)P_n(\cos\theta)\right| \quad (1)$$

where $P_0$ is the amplitude of the incoming plane wave, k is the wavenumber of the incoming sound wave, r is the distance between the sphere and the receiving transducer, θ is the angle between the incident wave and the scattered wave (180_ for our backscatter measurements), and $\delta_n$ are the phase-shifts of the n'th scattered wave. The phase shifts, $67_n$, are functions of ka, the Poisson's ratio of the sphere's material, and the ratio of the densities of the sphere to the surrounding fluid.

We assume that the backscatter of many spheres can be calculated from the backscatter due to one sphere if effects due to multiple scattering are ignored. In particular the scattering cross-section, $\eta_{tot}(f)$, from identical spheres with a number density n, is $$\eta_{tot}(f) n m_{sphere}(a,f) \qquad (2)$$

where $\eta_{sphere}$ is the scattering cross-section due to one sphere of size a. With the introduction of a distribution of n sizes, $w(a_n)$, the expression for the total scatter becomes $$\eta_{tot}(f) = \sum_n w(a_n) \eta_{sphere}(a_n, f). \qquad (3)$$

This expression was used in conjunction with the scatterer sizes to compute the theoretical predictions presented later in the paper. Values derived both from the manufacturer and the literature were used to compute the backscatter from the suspension. The values were a particle density of 1.055 g/cm³, density of Isoton of 1.0 g/cm³, a longitudinal speed of sound in Isoton of 1490 m/s, a longitudinal speed of sound in the polystyrene microsphere of 2380 m/s, and a shear velocity of the polystyrene microsphere of 1180 m/s. The value for the shear velocity of polystyrene is adjusted from previously reported values of 1100 to 1120 m/s in order to provide better agreement between experimental results and theoretical predictions.

Methods

A. Experimental

A series of measurements of the attenuation and backscatter of a suspension of polystyrene microspheres (Duke Scientific Corporation, CS03MC) were made in an experimental system designed for the purpose of measuring the properties of ultrasonic contrast agents. Seven distributions of polystyrene micropheres were used possessing mean diameters over the range of 30 to 100 μm in 10 μm steps. The polystyrene microspheres were sized with an optical particle sizer (AccuSizer™ 770, Particle Sizing Systems, Inc.) and found to possess distributions with half-widths of roughly 5% of their mean diameter. The particle sizer uses a single-particle optical sensing device. Particles in a liquid suspension are allowed to flow though a small photozone, i.e. a narrow, slab-like region of uniform illumination produced by light from a laser diode. Both the dilution of the particle suspension and the flow rate were adjusted to avoid coincidental particles in the photozone. The passage of a particle through the sensing zone causes a detected pulse, the magnitude of which depends on the mean diameter of the particle.

Figure 2:
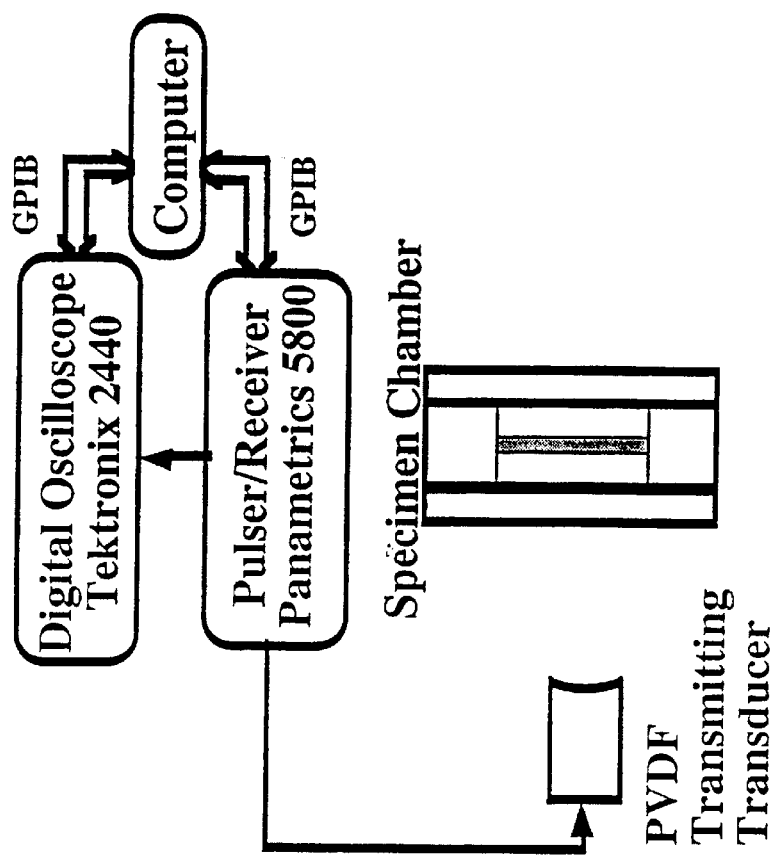
FIG. 2: The experimental setup used to make measurements of the apparent backscatter transfer function through a suspension of polystyrene microspheres.

A diagram of the experimental setup used to measure the attenuation of the polystyrene microspheres is presented in FIG. 2. A pulser/receiver (Panametrics 5800) was used to drive a broadband PVDF transducer (0.4 in. diameter, 3.25 in. focal length, Panametrics ZF3002-SU). A matched PVDF transducer received the signal and was connected to a high impedance channel of a digitizing oscilloscope (Tektronics 2440) via a short cable to minimize cable capacitance. The specimen chamber was positioned near the receiving transducer to minimize any phase distortion caused by the passage of the ultrasound through the suspension. The received wave form was digitized at 250 Megasamples/sec and transferred via an IEEE-488 bus to a computer (Macintosh Quadra 800) to be stored for off-line analysis. The speed of the bus allows for roughly 30 1024-point traces to be acquired each second. A total of 1000 traces were acquired for both attenuation and backscatter measurements.

Figure 3:
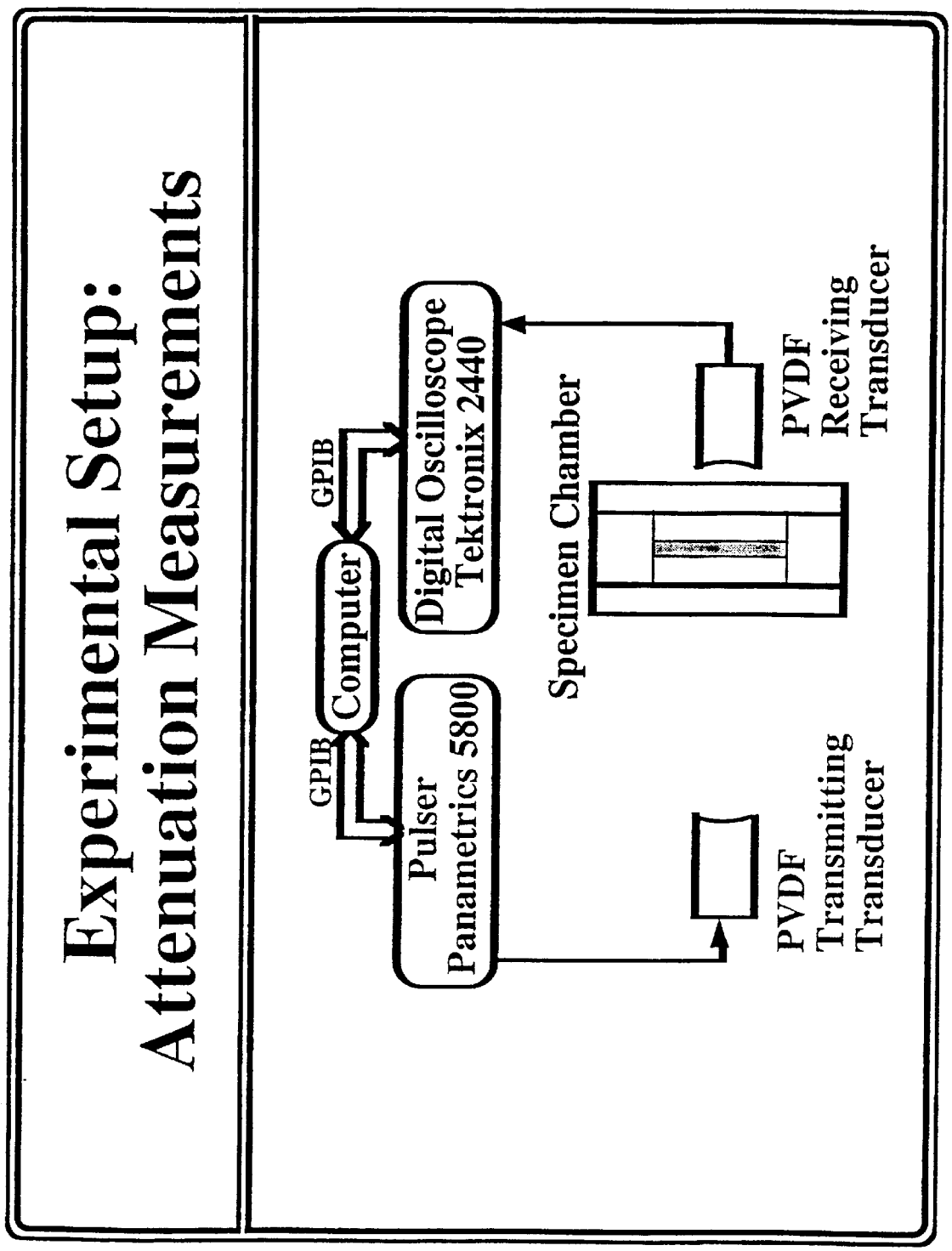
FIG. 3: The experimental setup used to make measurements of the signal loss (attenuation) through a suspension of polystyrene microspheres.

Measurements of the backscatter from the suspension were made with a similar setup shown in FIG. 3. A pulser/receiver (Panametrics 5800) was used to drive a broadband PVDF transducer (0.4 in. diameter, 3.25 in. focal length, Panametrics ZF3002-SU). The transducer was placed so that the focal region occurred after the echo from the front wall of the specimen chamber. In the focus of a transducer, the insonifying waves are roughly constant in amplitude and phase which allows for several simplifications in the data reduction technique. The backscattered signal was amplified by 40dB using the Panametrics 5800. The waveform was then captured by a digitizing oscilloscope and sent to the computer.

Referring now to the specimen chamber shown in FIG. 1, the chamber consists of two acoustic windows made of SaranWrap™ held by two Lexan® pressure plates. A micropipette was fixed to a piece of Tygon™ tubing attached to one port of the chamber and was used to agitate the suspension of microspheres throughout the measurement. The constant agitation allowed for a new ensemble of scatterers to be measured with each insonification. The spatial distribution of the scatterers was found to be uniform throughout the chamber by examining the picture from a medical imaging system and by optical inspection of the chamber. For the purpose of calibration, a steel plate was substituted for the microspheres below the acoustic window. The backscattered signal from the steel plate was used in the calculation of the apparent backscatter transfer function described below.

B. Data Reduction

A first-order, broadband data reduction method was employed to reduce the measurements of the backscatter and attenuation to the inherent backscatter coefficient of a distribution of spherical scatterers. The raw or backscattered signal can be thought of as a convolution of effects due to the electro-mechanical response of the transducer and accompanying electronics, the effects of the frequency-dependent beam volume, the attenuation due to the suspension, and the inherent scattering of the suspension. In order to compensate for the effects due to the electronics, the backscattered signal was compared to the signal returned from a polished steel reflector. By normalizing the spectra returned from the suspension by the spectrum of the steel plate reflection, the effects of the measurement system can be removed.

The effect of the frequency-dependent beam volume and attenuation can be removed by making several simplifications. The first simplification is that the beam volume is defined laterally by the frequency dependent beam width and along the beam axis by the gate duration. The second simplification, that the scatterers are uniformly distributed throughout the scattering volume, was verified with a medical imager and by visual inspection. Using both of these approximations, the backscatter coefficient can be expressed as $$\eta(f) = \frac{\Gamma^2}{4T^4} R^2 F(\alpha, \tau) \frac{1}{V(f)} \langle |S(f)|^2 \rangle \qquad (4)$$

where $\eta(f)$ is the frequency dependent backscatter coefficient, $\Gamma$ is the amplitude reflection coefficient of our polished steel reflector, T is the transmission coefficient between the water and the suspension of the polystyrene microspheres, R is the focal length of the transducer, V(f) is the frequency dependent beam volume, S(f) is the apparent backscatter transfer function of our suspension, and F(α, τ) is an attenuation correction factor. F(α, τ) can be expressed $$F(\alpha, \tau) = e^{4\alpha(f)x} e^{\alpha(f)c\tau} \frac{2\alpha c\tau}{e^{\alpha c\tau} - e^{-\alpha c\tau}} \quad (5)$$

where α is the frequency dependent attenuation of the suspension, c is the speed of sound within the suspension, x is the position of the window after the front wall of the chamber, and τ is the gate duration. This data reduction method is used to compare experimental results with theoretical predictions of the scattering due to an ensemble of spherical scatterers.

C. Data Anialysis

The apparent backscatter transfer function was calculated by applying a 2.56 μsec Hamming window to the trace at a position of 1.0 μsec after the echo from the chamber wall. Other combinations of window position and length yielded similar results when reduced to backscatter coefficient. The power spectra of the gated traces were calculated, normalized by the power spectrum of a polished stainless steel plate, and averaged.

The apparent attenuation coefficient was calculated from ten measurements of the through-transmitted signal when the suspension was in the chamber. Each measurement consisted of 100 time domain averages of the waveform. A calibration trace was taken by filling the chamber with Isoton™, a saline-buffered solution, and measuring the through-transmitted pulse. The power spectra of the 10 averaged suspension-path trace s were subtracted from the power spectruem of the saline-path trace to yield signal loss as a function of frequency. The attenuation coefficient was measured by normalizing the signal loss by the chamber thickness which was found using a standard pulse/echo method.

Results

Figure 4:
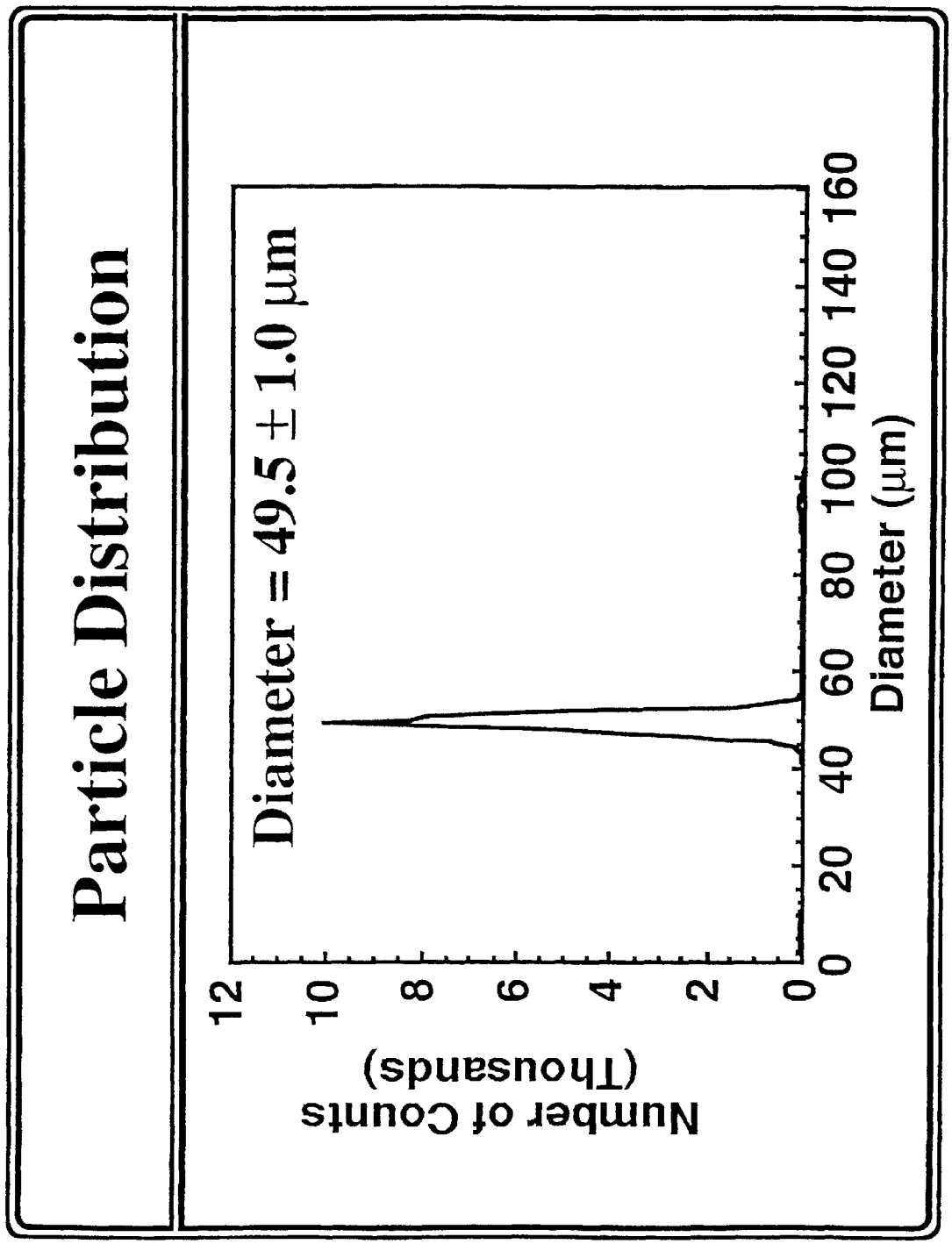
FIG. 4: A typical distribution of polystyrene microspheres having a mean diameter of 49.5 $\mu$m and a standard deviation of 1.0 $\mu$m.

FIG. 4 shows the distribution of sizes of polystyrene microspheres found by optically sizing the microspheres having a nominal diameter of 50 μm. The mean diameter measured was 49.5 μm with a width at half-maximum of 1.0 μm, which allowed measurement of sharp resonances in the backscatter coefficient.

Figure 5:
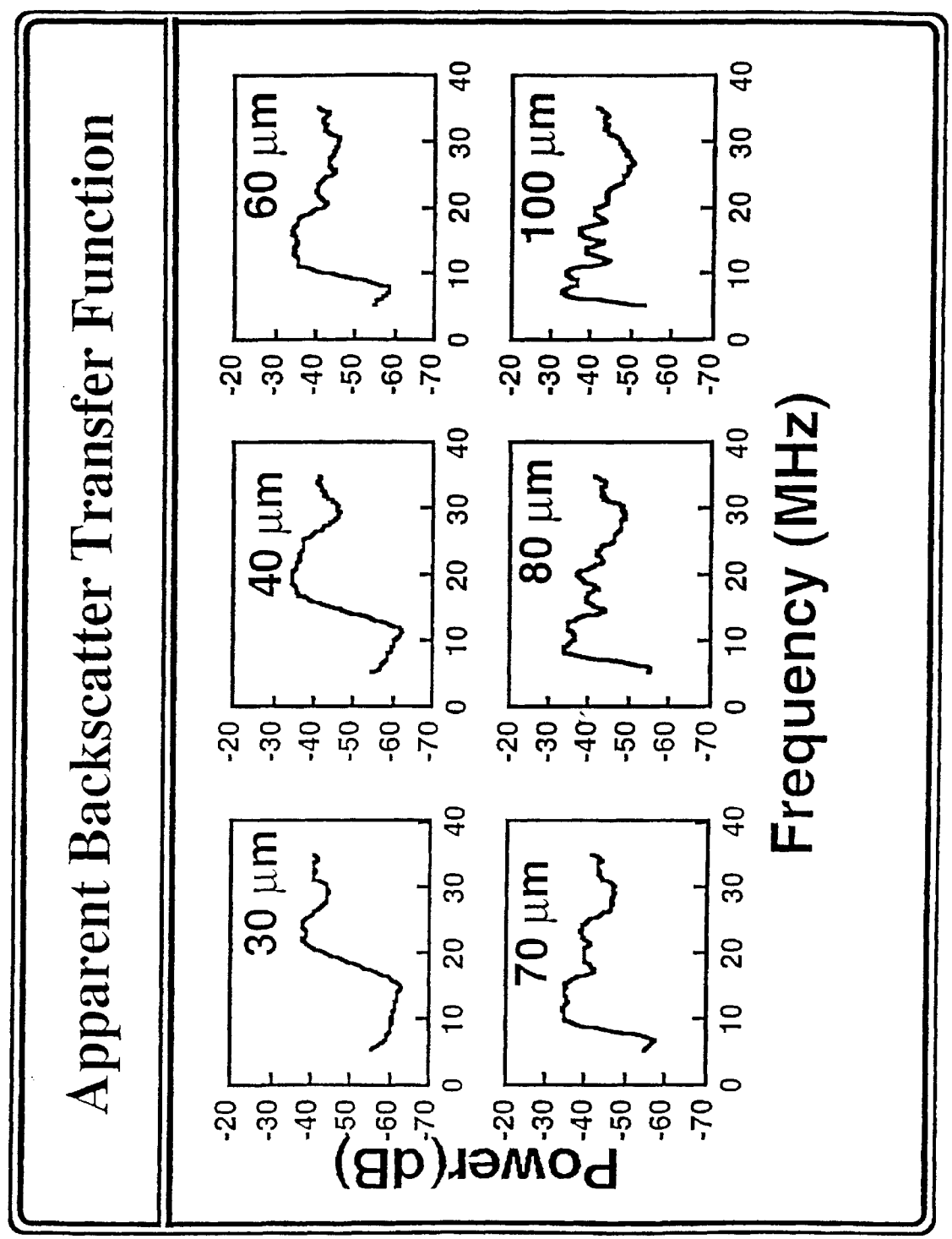
FIG. 5: The top panel shows the usable bandwidth of a typical apparent backscatter transfer function for polystyrene microspheres with a mean diameter of 49.5 $\mu$m. The middle panel shows the corresponding measurement of the apparent attenuation. The bottom panel is the resulting backscatter coefficient. All error bars represent the standard deviation of the measurements.

FIG. 5 illustrates a typical apparent backscatter transfer function, apparent attenuation coefficient and the experimental measurements of the backscatter coefficient. The top and middle graphs are direct measurements of backscatter and attenuation respectively while the lower of the graphs is the reduced form of backscatter coefficient as described above. All error bars represent the standard deviation of the measurements.

Figure 6:
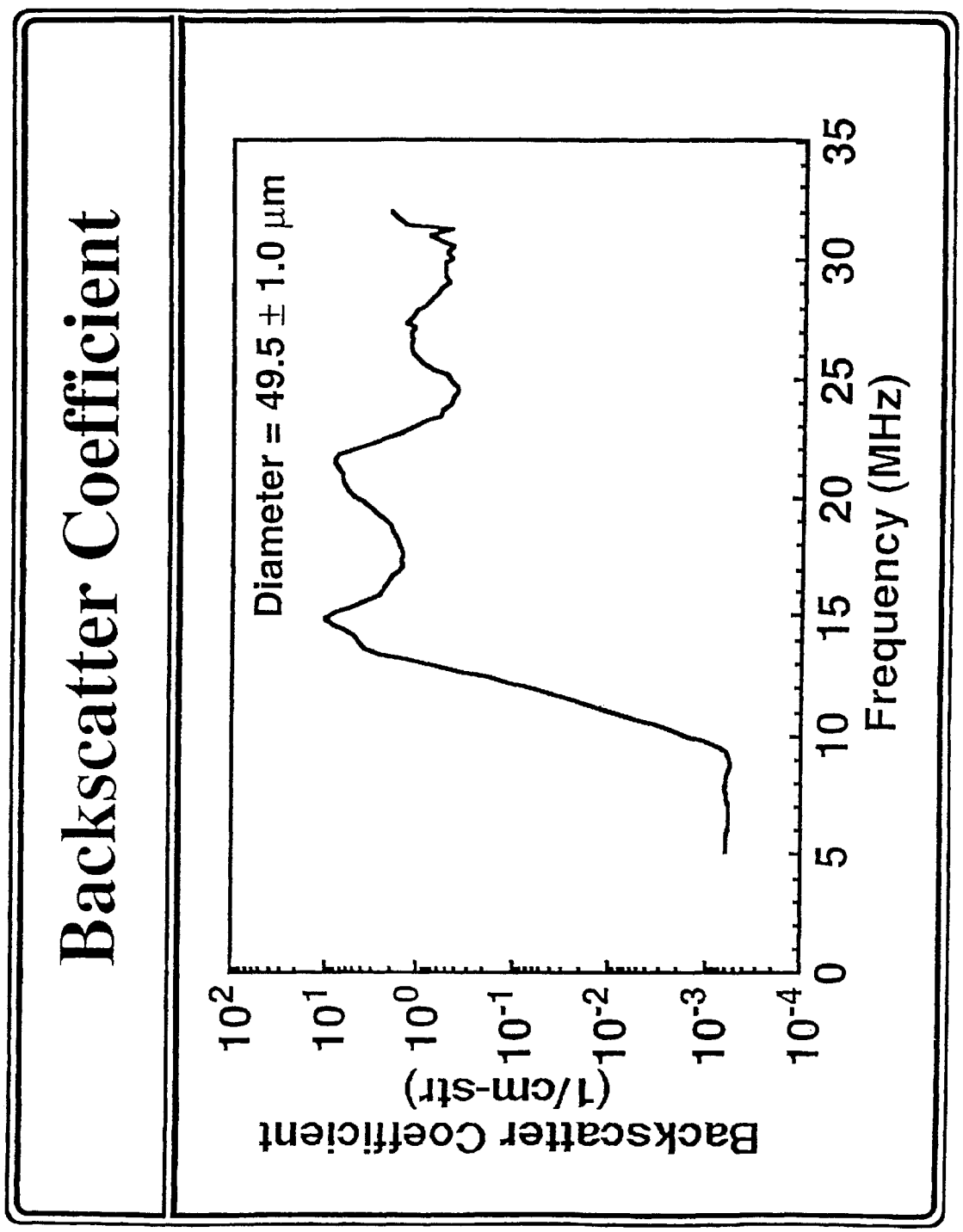
FIG. 6: The predicted backscatter coefficient of a single-sized ensemble of microspheres and of the distribution of microsphere sizes shown in FIG. 3.

The effect of introducing a distribution of scatterer sizes into the theoretical predictions of the scattering model is shown in FIG. 6. The theoretical predictions were made with the use of Equation (3) where the distribution, w($a_n$), was calculated from the data in FIG. 3. Each individual microsphere diameter will exhibit its own series of resonances, so the effect of introducing a distribution of scatterer diameters averages the resonances together causing a broadening of the resonances.

Figure 7:
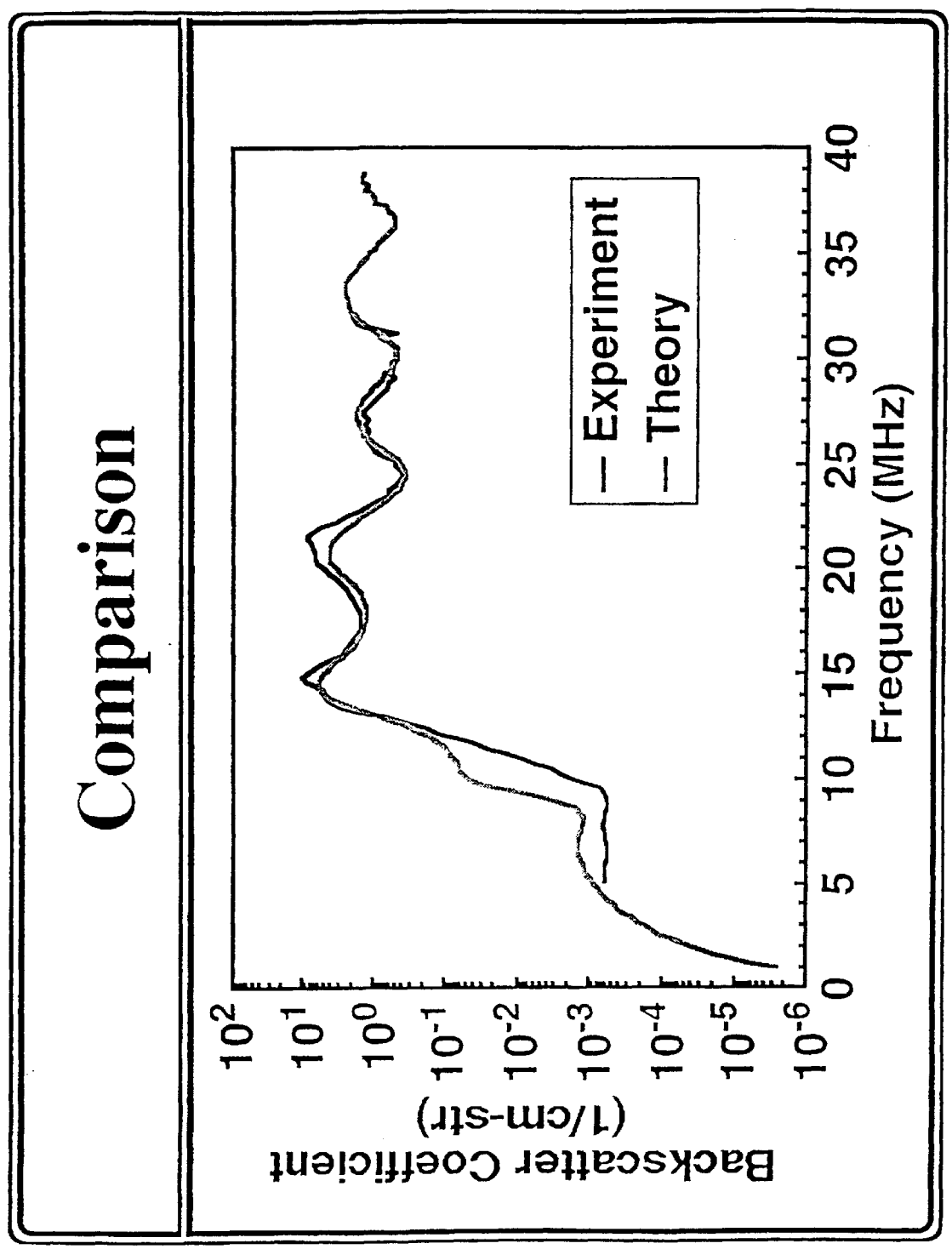
FIG. 7: Comparison of the theoretically predicted values of the backscatter coefficient with the experimental results.

FIG. 7 compares the experimentally measured backscatter coefficient and the theoretical predictions of the scattering model for a variety of suspensions of narrowly distributed microsphere diameters. Agreement between experiment and theory was quite good although there are several discrepancies in the magnitude of the backscatter coefficient near the resonances in the backscatter spectrum.

Discussion

A broadband, single transducer pair experimental system has been developed for measuring the physical properties of ultrasonic contrast agents. The system has been used successfully to measure the backscatter coefficient of suspensions of polystyrene microspheres in the frequency range from 5 to 35 MHz. The use of a single transducer pair for broadband measurements is advantageous for several reasons. It allows quick and reliable investigations of time-varying substances such as contrast agents. Also, the compensation for the effects of the transducer's beam profile and focus are similar for each set of measurements because knowledge of only one set of transducer characteristics is necessary.

The ability to make reliable measurements of polystyrene microspheres over such a broad bandwidth suggests that a preparation of suspended and agitated spheres may be a useful in vitro calibration device for high frequency ultrasound systems. This experimental system may serve as a useful calibration device for several reasons, some of which have been previously investigated by others in connection with tissue-mimicking phantoms. However, we have introduced a novel mixing technique which leads to improved ensemble averaging of the backscatter in contrast to the spatial averaging required with the use of a conventional phantoms with stationary scatterers.

There are several reasons why a suspension of particles might provide a better calibration device than a steel plate. The backscatter is returned from a volume of the suspension while the backscatter from a steel plate represents only a planar reflection of the insonifying wave. Unlike the extremely high amplitude of the reflection from a polished steel plate, the scatter from a suspension of spheres is of the same order of magnitude as the scatter from within a volume of tissue. The use of such microspheres thereby permits calibration of the ultrasound system over the range of amplitudes for which it will be used in vivo. This may facilitate calibration of high frequency scan heads or intravascular ultrasound catheters before each use and allow comparisons between studies conducted at different times or by different investigators or clinicians. Suspensions of solid, elastic spheres may also prove useful in the area of acoustic microscopy. The current standard for calibration is the reflection from a polished stainless steel plate which is sensitive to alignment of the surface of the plate. Alignment is not as crucial an issue when measuring backscatter for a suspension of spheres because of the symmetry of the fundamental scatterer.

In the area of ultrasound contrast agents, tightly-sized polystyrene spheres provide a possible calibration for both future in vivo and current in vitro measurements of the effects of contrast agents. Suspensions of the spheres could be used in an in vitro setting to calibrate the ultrasonic measurement system before injection of the contrast agent. In addition, our techniques may be extendible to the measurement of the properties of specific contrast agents. In fact, the use of contrast agents in vivo as a possible calibration tool for the longitudinal study of a patient is an area of interest and may even provide a method to compare acoustic measurements between different patients if effects due to lung filtration and bubble destruction can be taken into account.

We examined the backscatter from a suspension of polystyrene microspheres with diameters ranging from 30 μm to 100 μm. In the field of medical ultrasonic contrast agents, sizes below 10 μm are required to pass through the vascular bed of the lungs. However, the agreement between measurements of the backscatter coefficient and theoretical predictions shows the feasibility of making direct measurements of contrast agents with our experimental setup. We assumed that the concentrations we studied lie within the single-scattering regime and that little or no multiple-scattering occurs. This assumption may be valid because the magnitude of the scatter is relatively small, and hence any multiple scattering would not contribute significantly to the final measure of backscatter. Another limitation was use of only a single concentration of microspheres for each size range. It has been shown by other researchers that the scatter from suspensions of solid spheres exhibits strong temperature dependence. We maintained the water bath at a constant temperature during the course of a measurement for each size of microspheres, although the temperature between measurements varied by as much as 1.6 C. For the purpose of using suspended particles as a calibration standard, careful control of the temperature would be necessary.

In the model, the positions of the resonances in the backscatter coefficient spectrum are very sensitive to the value chosen for the transverse velocity of the material which makes up the scatterers. In the case of polystyrene microspheres, a range of transverse velocities has been reported which vary from 1100 to 1120 m/s. In this study, we chose a value of 1180 m/s in order to adjust the "theoretical" resonances to overlap with our measured resonances. Independent of scatterer size, the same transverse velocity of 1180 m/s resulted in theoretical predictions that agreed with experimentally measured resonances. The discrepancy between the values of transverse velocity for polystyrene reported in the previous literature and those measured in this study could be due to several factors. The polystyrene microspheres were reported by the manufacturer to have a mixed chemical make-up of polystyrene and polystyrene divinylbenzene, a system which has not been well characterized ultrasonically.

The data presented in this study also suggest that the use of a simple, first-order, broad-band reduction technique for the backscatter coefficient yields quantitatively good agreement with theoretical predictions. At high frequencies, the depth of field of a focused ultrasonic transducer is extremely small, and has led many researchers to study the use of sophisticated correction techniques for modeling the ultrasonic beam as a function of frequency and space. The apparent agreement between the measurements presented here and the theoretically calculated values for backscatter suggests that a simpler approach to modeling the beam volume might be adequate for many measurements in this frequency range.

The ability to make reliable measurements of polystyrene microspheres over a broad bandwidth suggests that such a preparation of suspended spheres may prove to be a useful calibration device for high frequency ultrasound systems.

What is claimed is:

1. A method for calibrating an ultrasound system comprising the steps of:

providing a suspension of microspheres of a selected size distribution in a container having at least one acoustic aperture, the microspheres being suspended in a liquid environment;

placing the container in a constant temperature water bath;

continuously agitating the suspension of microspheres in the container while simultaneously measuring the backscatter from the suspension of microspheres; and calibrating the ultrasound system to a selected backscatter setting in accordance with the measured backscatter.

2. The method of claim 1 wherein the microspheres are solid.

3. The method of claim 1 wherein the microspheres are hollow.

4. The method of claim 1 wherein the microspheres are solid polystyrene beads.

5. The method of claim 1 wherein the suspension of microspheres are continuously agitated by a means for pumping the liquid environment containing the suspension of microspheres.

6. The method of claim 5 wherein the means for pumping the liquid environment containing the suspension of microspheres is a manual or mechanical pump.

7. The method of claim 1 wherein the suspension of microspheres are continuously agitated by a means for mixing the liquid environment containing the suspension of microspheres.

8. The method of claim 1 wherein the suspension of microspheres are continuously agitated by a means for stirring the liquid environment containing the suspension of microspheres.

* * * * *